United States Patent
Nakashima et al.

(10) Patent No.: US 7,390,677 B2
(45) Date of Patent: Jun. 24, 2008

(54) IMMUNOASSAY AND IMMUNOASSAY APPARATUS

(75) Inventors: Kazuhiro Nakashima, Miki (JP); Tsuneyoshi Torii, Kobe (JP); Hiroshi Tsuchiya, Kobe (JP); Shinya Uchida, Kobe (JP); Aya Konishi, Kobe (JP); Kunio Tanaka, Kakogawa (JP)

(73) Assignee: Sysmex Corporation, Kobe-Shi (JP)

( * ) Notice: Subject to any disclaimer, the term of this patent is extended or adjusted under 35 U.S.C. 154(b) by 347 days.

(21) Appl. No.: 10/019,949

(22) PCT Filed: Jun. 11, 2001

(86) PCT No.: PCT/JP01/04917

§ 371 (c)(1),
(2), (4) Date: Jan. 7, 2002

(87) PCT Pub. No.: WO01/96868

PCT Pub. Date: Dec. 20, 2001

(65) Prior Publication Data

US 2003/0082662 A1 May 1, 2003

(30) Foreign Application Priority Data

| Jun. 12, 2000 | (JP) | ............................. 2000-175914 |
| Jun. 14, 2000 | (JP) | ............................. 2000-179058 |
| Aug. 3, 2000 | (JP) | ............................. 2000-236199 |

(51) Int. Cl.
*G01N 33/546* (2006.01)

(52) U.S. Cl. ............................. 436/533; 436/10; 436/16; 436/164; 436/175; 436/528; 436/529; 436/533; 436/534; 436/536; 436/7.1; 436/287.2; 436/962

(58) Field of Classification Search ................. 436/533, 436/523–529, 531–534, 165, 514, 536, 538, 436/10, 16, 164, 175; 435/7.21, 7.25, 7.8, 435/7.1, 287.2, 962; 356/335, 336
See application file for complete search history.

(56) References Cited

U.S. PATENT DOCUMENTS 4,279,506 A * 7/1981 Maines .......................... 356/39
(Continued)

FOREIGN PATENT DOCUMENTS

JP 10-48214 2/1998
(Continued)

OTHER PUBLICATIONS

Certified translation of Etsuro Shinkai et al., Sysmex Journal, vol. 20, No. 1, pp. 77-80, (1997).
(Continued)

*Primary Examiner*—Gailene R. Gabel
(74) *Attorney, Agent, or Firm*—Birch, Stewart, Kolasch & Birch, LLP

(57) ABSTRACT

An immunoassay comprises the steps of: (a) mixing a whole blood sample with sensitized insoluble carrier particles smaller than erythrocytes to cause an immune agglutination reaction; (b) introducing the resulting immune agglutination reaction mixture including agglutinated particles and unagglutinated particles to a flow cell, irradiating the particles passing through the flow cell with laser light, and detecting scattered lights generated thereby; (c) setting a threshold value for distinguishing unagglutinated particles from agglutinated particles and a threshold value for distinguishing the agglutinated particles from blood cells with regard to intensity of the scattered light; and (d) distinguishing and counting the unagglutinated particles, the agglutinated particles and the blood cells from the scattered lights detected in the step (b), in reference to the threshold values set in the step (c).

10 Claims, 6 Drawing Sheets

U.S. PATENT DOCUMENTS

| | | | | |
|---|---|---|---|---|
| 5,527,714 | A | * | 6/1996 | Kosako ...................... 436/534 |
| 5,854,005 | A | * | 12/1998 | Coller ....................... 435/7.21 |
| 6,030,845 | A | * | 2/2000 | Yamao et al. ............... 436/533 |
| 2001/0046685 | A1 | * | 11/2001 | Moskowitz et al. ........ 435/7.21 |

FOREIGN PATENT DOCUMENTS

WO      WO 98/20351    *   5/1998

OTHER PUBLICATIONS

PAMIA-30 Scientific Information, pp. 1-36, 1994.

* cited by examiner

IMMUNOASSAY AND IMMUNOASSAY APPARATUS

This application is the national phase under 35 U.S.C. § 371 of PCT International Application No. PCT/JP01/04917 which has an International filing date of Jun. 11, 2001, which designated the United States of America.

TECHNICAL FIELD

The present invention relates to an immunoassay and immunoassay apparatus, more particularly an immunoassay by use of flow cytometry for analyzing a sample subjected to immune agglutination and immunoassay apparatus.

BACKGROUND ART

For immunoassays on infection disease-related test items, serum has been used as a sample to be tested. However, it takes about 30 minutes to separate serum from whole blood, including time for blood coagulation and time for subsequent centrifugation.

Typical examples of immunoassays include a radioimmunoassay (RIA), an enzyme immunoassay (EIA) a particle agglutination immunoassay and a counting immunoassay. However, RIA and EIA need B(Bound form)/F(Free form) separation after antigen-antibody reaction, and therefore, require time and labor before the results of the assays are obtained.

A particle agglutination immunoassay is advantageous in that it requires only the mixing of a sample to be tested with a suspension of insoluble carrier particles (e.g., latex) sensitized with an antibody or an antigen. Therefore it does not require the B/F separation and can be performed by simple operation.

Further, a counting immunoassay which is used serum or blood plasma and is known as an assay for measuring the degree of particle agglutination, antigen- or antibody-combined latex particles are reacted with an antibody or an antigen in a sample, so that they agglutinate according to the amount of the antigen or antibody. Agglutinated latex particles are distinguished by their size and counted. The count of unagglutinated latex particles is represented by M (monomer), the count of at least two agglutinated latex particles is represented by P (polymer), and the sum of M and P is represented by T (total). P/T is calculated as a degree of agglutination. If a calibration curve is determined beforehand by measuring the degree of agglutination of a known concentration of an antigen or antibody, the amount of the antigen or antibody in the sample can be found from the degree of agglutination of the sample (Sinkai Etsuro et al.: Principle of Measurement of PAMIA, Sysmex J. Vol. 20, No. 1, p.p. 77-78 (1997)). Since the agglutinated particles are directly counted, this assay is more accurate than the turbidimetric immunoassay which detects optical changes in the entire test sample.

In recent years, however, it has become necessary to judge rapidly whether or not a patient is infected with virus hepatitis, HIV or the like, for example, in the case of emergency operation. Accordingly, it is demanded that test time from collection of blood up to obtainment of test results be shortened. Also there is demanded a simple immunoassay that realizes the obtainment of highly accurate test results.

Taking the shortening of the test time into consideration, it is more desirable to use whole blood collected from a patient than to use serum, as a sample for immunoassays.

For example, Japanese Unexamined Patent Publication No. HEI 10(1998)-48214 proposes a whole blood assay using a conventional latex agglutination method. According to this assay, a whole blood sample is hemolyzed and the resulting sample is tested on its immune reaction by a latex turbidimetric immunoassay. This assay can provide test results simply and rapidly.

However, according to this assay, since the whole blood is hemolyzed, hemoglobin or fragments of hemolyzed blood cells interfere with the turbidimetric immunoassay using optical means and limit the accuracy of the assay. Therefore, the assay is not suitable for cases which require relatively high accuracy, for example, infection disease-related test items.

Whole blood usually contains about 40 to 50% of blood cell components in terms of hematocrit value. If whole blood is used in the same amount as in the case where serum is used, its measured values become lower than the values obtained by serum, reflecting the amount of blood cell components (a blood cell volume ratio content). In order to obtain measured values equivalent to those obtained by serum measurement, the values need to be corrected for the blood cell volume ratio content.

For this purpose, in Japanese Unexamined Patent Publication No. HEI 10 (1998)-48214, the hematocrit value is separately measured, and the measured values are corrected for the measured hematocrit value.

However, it is complicated to measure blood cells separately for correction. To avoid this, an inmmunoassay apparatus may be provided with a blood cell counting section and an immunoassay section, but such an apparatus becomes complicated and expensive. Therefore, there is a demand for a method for estimating or correcting influence by blood cells only by the immunoassay section.

Fully automated immunoassay apparatuses currently used are mostly designed for assaying serum (or blood plasma) samples, and therefore, do not have a stirrer which is necessary for assaying whole blood samples. If such apparatuses are used for immunoassays of whole blood samples, the blood cell components settle and only supernatant is used. The measured values are not affected seriously by the hematocrt value and may be not shifted apart to lower values.

In this case, if measured values are corrected for the hematocrit value separately measured by a blood cell counter for whole blood measurement as disclosed in Japanese Unexamined Patent Publication No. HEI 10 (1998)-48214, the measured values shift apart to higher values. As a result, precise measurement results cannot be obtained.

Alternatively, in an apparatus for both whole blood samples and serum samples which is already available commercially, a measuring sequence, an analysis program and the like are usually changed for measurement of a whole blood sample by designating the "whole blood measurement" on operation panel of the apparatus. However, where the number of samples is large, it is time- and labor-consuming to designate the "whole blood measurement" every time when a whole blood sample is used, and, where whole blood samples and serum samples are both used, it is also time- and labor-consuming to re-designate every time when the types of samples are changed. Furthermore, if the type of a sample is mis-designated, accurate measurement results are not obtained.

DISCLOSURE OF INVENTION

An object of the present invention is to provide a method which can perform a highly accurate immunoassay on a whole-blood sample without need to hemolyze the whole blood sample or separate serum therefrom, a method which allows simple correction for the hematocrit content.

The present invention provides an immunoassay comprising the steps of:

(a) mixing a whole blood sample with sensitized insoluble carrier particles smaller than erythrocytes to cause an immune agglutination reaction;

(b) introducing the resulting immune agglutination reaction mixture including agglutinated particles and unagglutinated particles to a flow cell, irradiating the particles passing through the flow cell with laser light, and detecting scattered lights generated thereby;

(c) setting a threshold value for distinguishing unagglutinated particles from agglutinated particles and a threshold value for distinguishing the agglutinated particles from blood cells with regard to intensity of the scattered light; and (d) distinguishing and counting the unagglutinated particles, the agglutinated particles and the blood cells from the scattered lights detected in the step (b), in reference to the threshold values set in the step (c).

The present invention also provides an immunoassay apparatus for realizing a immunoassay of the present invention comprises:

a reaction part for mixing a whole blood sample with sensitized insoluble carrier particles smaller than erythrocytes to cause an immune agglutination reaction;

a dispensing mechanism for introducing the resulting immune agglutination reaction mixture including agglutinated particles and unagglutinated particles to a flow cell, a laser for irradiating the particles passing through the flow cell with laser light, and a photo acceptance unit for detecting scattered light generated thereby, signal processing means for converting a light signal to an electrical signal, data processing means for setting a threshold value for distinguishing unagglutinated particles from agglutinated particles and a threshold value for distinguishing the agglutinated particles from blood cells with regard to signal based on intensity of the scattered light; and for distinguishing and counting the unagglutinated particles, the agglutinated particles and the blood cells according to the set threshold values.

BEST MODE FOR CARRYING OUT THE INVENTION

Figure 1:
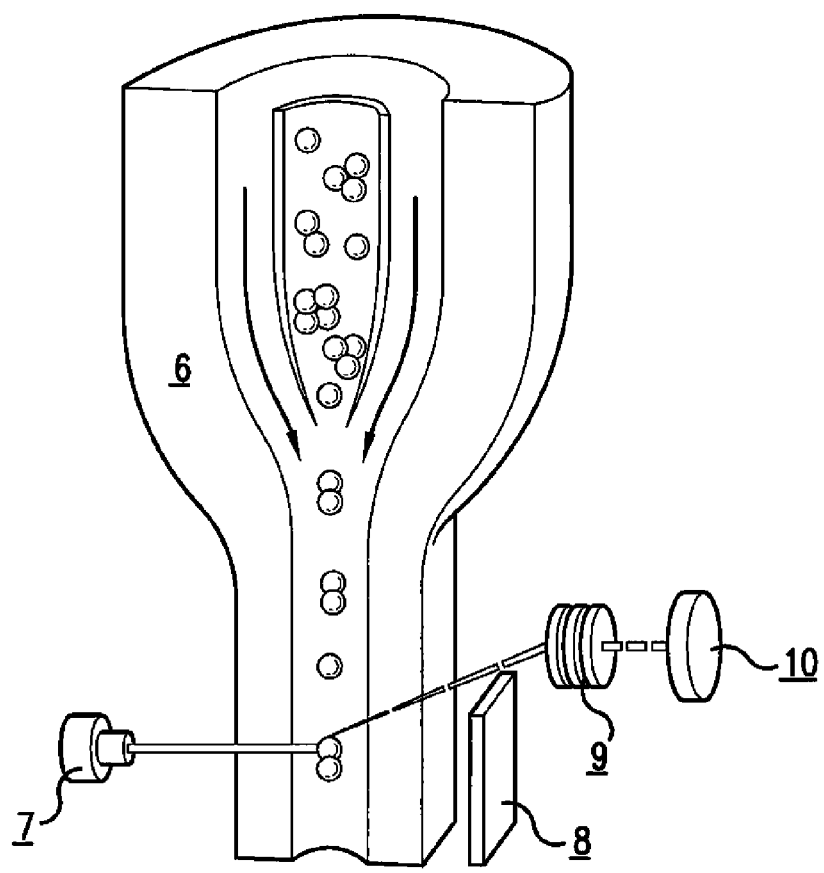
FIG. 1 illustrates a measurement principle of a whole blood immunoassay in accordance with the present invention.

In the immunoassay of the present invention, first, in Step (a), the whole blood sample is mixed with insoluble carrier particles so that the immune agglutination reaction takes place. In the present invention, the immunoassay generally means measurement of the degree of agglutination of an antigen or antibody, the concentration of an antigen or antibody and the like. The whole blood sample usually means blood collected from a human being or other animals but not subjected to serum or plasma separation. However, before the immunoassay of the present invention is carried out, the whole blood sample may be anticoagulated and/or diluted with a reaction buffer and the like.

As anticoagulants used for anticoagulating the sample, usable are those usually used for blood tests such as EDTA salt, citrates and the like. As the reaction buffer, usable is a phosphate buffer or Tris-HCl buffer, for example. The pH of the reaction buffer may suitably be about pH 6 to 8.5. The osmotic pressure of the reaction buffer may suitably be such that erythrocytes are not lyzed and preferably be 150 mOsm/kg or more. To the reaction buffer, a substance suppressing a non-specific reaction, a sensitizer and the like may be added as required. The mixture of the whole blood with the reaction buffer may be for preparation for the subsequent immune agglutination reaction. When the whole blood is diluted with the reaction buffer, the dilution ratio may suitably be about 5 to 100 (by volume) and may preferably be 10 to 50. Temperature and time at and during which the whole blood is mixed with the reaction buffer may suitably be about 20 to 50° C. and about 1 to 5 minutes.

The insoluble carrier particles may be particles immunized, i.e., sensitized with an antigen or antibody. As materials for the particles, synthetic polymers, typically polystyrene latex or the like may be mentioned, for example. The particles suitably have such a size that allows the particles to be distinguished from blood cells, especially, erythrocytes. Since the size of erythrocytes is about 7 to 8 μm in average particle diameter in plan view and about 2.2 μm in thickness, the insoluble carrier particles suitably have a diameter of about 0.1 to 1.0 μm. The particles are preferably uniform.

The insoluble carrier particles can be sensitized by a method known in the field of art, for example, by physical adsorption, chemical binding, etc. The antigen or antibody used for sensitizing the particles is not particularly limited so long as it can be detected by utilizing antigen/antibody reaction. The insoluble carrier particles are usually used in a suspension thereof in a solvent, which may suitably be water, the above-mentioned buffer or the like. The mixing ratio of the insoluble carrier particles to the solvent is suitably about 0.1 to 1 w/v %.

As regards the immune agglutination reaction, the above suspension containing sensitized insoluble carrier particles is added to the whole blood sample optionally diluted with the reaction buffer so that an antigen/antibody reaction takes place. Here, the above suspension is used in such an excess amount that the intended agglutination reaction takes place sufficiently. The temperature is suitably 20 to 50° C., and the time is suitably 15 seconds to 20 minutes.

In Step (b), scattered lights from the resulting agglutination reaction mixture are detected.

For detecting the scattered light, it is suitable to use an apparatus which can detect the scattered lights for counting blood cells. Preferably, the apparatus is also provided with means for immunoassay in which the blood cell components do not affect the reaction system, simultaneously with the counting of blood cells. For example, a PAMIA series produced by Sysmex Corporation provides measuring apparatuses for counting immunoassay utilizing the principle of flow cytometry. This series is suitable because a single apparatus can perform both an immunoassay (latex agglutination) and blood cell counting according to the following procedure.

Figure 10:
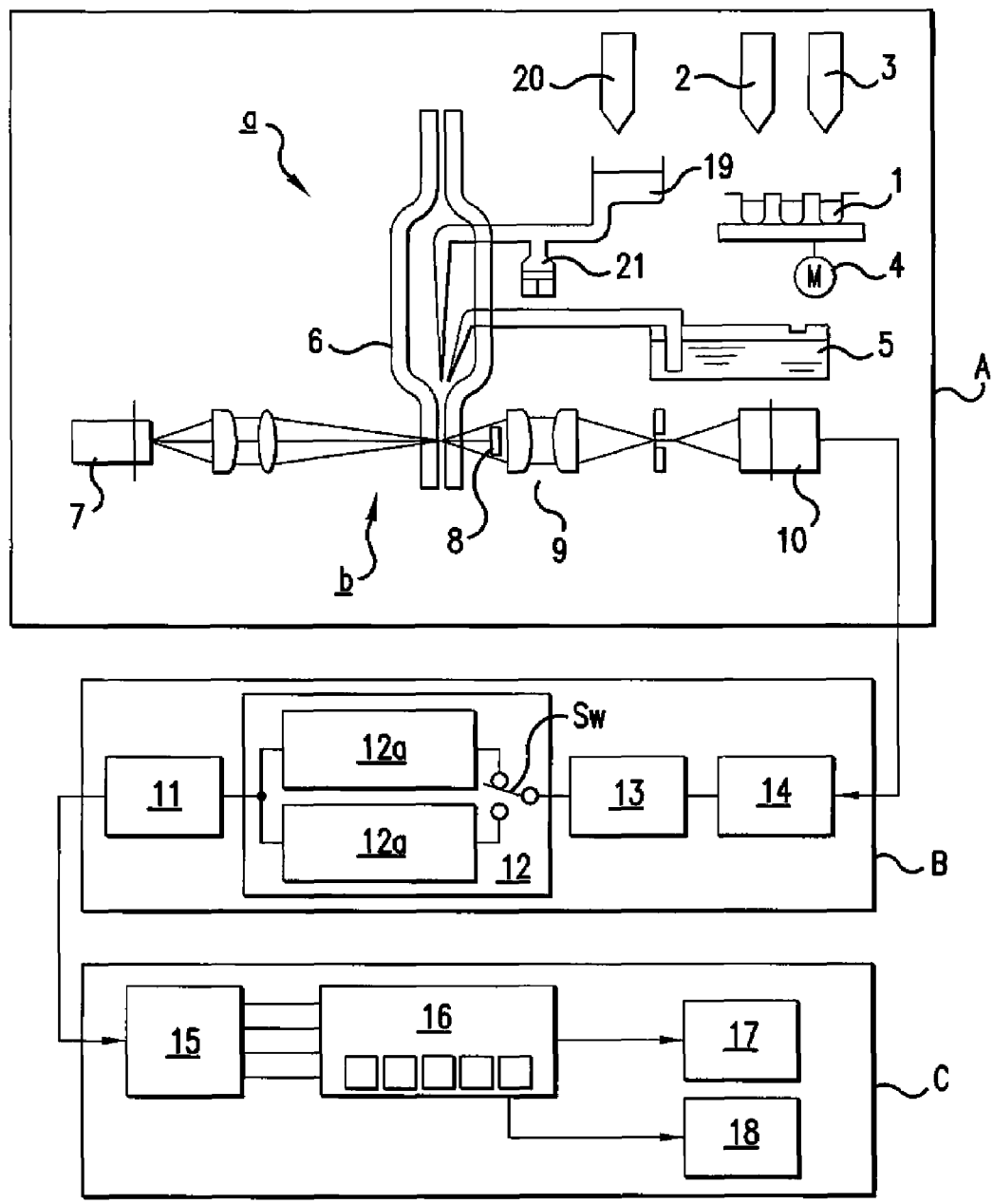
FIG. 10 is a schematic block diagram illustrating an apparatus for realizing the immunoassay of the present invention.

More particularly, an apparatus for realizing the immunoassay of the present invention includes a particle detecting block A, a signal processing block B and a data processing block C., as shown in FIG. 10.

The particle detecting block A is composed mainly of a sample supply section a and a particle detecting optical means b.

The sample supply section a is provided with a reaction part such as a reaction plate 1; a dispensing mechanism 2,3 such as a pipette for dispensing a blood sample, insoluble carrier particles and optionally a diluent into wells of the reaction plate; and optionally an oscillating mechanism 4 such as an eccentric motor for oscillating the reaction plate. The sample supply section a is further provided with a dispensing mechanism 20 for dispensing the reaction mixture to a chamber 19 and sample feed means 21 such as a sheath syringe for feeding the reaction mixture in the chamber 19 to the particle detecting optical means b.

The particle detecting optical means b is provided mainly with a flow cell 6, a semiconductor laser 7, a beam stopper 8, a lens and a photo acceptance unit 10 as shown in FIG. 1.

The signal processing block B is provided with a filter buffer 11, a function amplification circuit 12, an emitter 13, an amplifier 14 and/or the like, as required. The function amplification circuit may be so constructed that a linear amplifier 12a, a logarithmic amplifier 12b and the like can be switched by actuation of a switch.

The data processing block C is composed of a discrimination circuit 15, a microcomputer (including a means for counting the number of signals representative of particles discriminated by size, an arithmetic means for calculating the agglutination ratio from the number of counted signals, a control means for samples and a means for controlling the drive of the particle detecting block, for example) 16, a display 17, a printing circuit 18 and/or the like, as required.

In other words, an immunoassay apparatus for realizing the immunoassay of the present invention comprises:

a reaction part for mixing a whole blood sample with sensitized insoluble carrier particles smaller than erythrocytes to cause an immune agglutination reaction;

a dispensing mechanism for introducing the resulting immune agglutination reaction mixture including agglutinated particles and unagglutinated particles to a flow cell, a laser for irradiating the particles passing through the flow cell with laser light, and photo acceptance unit for detecting scattered light generated thereby, signal processing means for converting a light signal to an electrical signal, data processing means for setting a threshold value for distinguishing unagglutinated particles from agglutinated particles and a threshold value for distinguishing the agglutinated particles from blood cells with regard to signal based on intensity of the scattered light; and for distinguishing and counting the unagglutinated particles, the agglutinated particles and the blood cells according to the set threshold values.

The apparatus for realizing the immunoassay apparatus of the present invention further comprises: data processing means for calculating a degree of agglutination from the number of the unagglutinated particles and the number of the agglutinated particles, converting the degree of agglutination into the concentration of an antigen or antibody in the whole blood sample using a calibration line produced beforehand; and correcting the concentration of the antigen or antibody according to the number of the blood cells.

For the detection of the scattered light from the agglutination reaction mixture including agglutinated particles and unagglutinated particles, the reaction mixture is first diluted to adjust the concentration of the particles suitably for counting, subsequently the diluted reaction mixture is extruded little by little into a laminar flow of a sheath liquid formed in a flow cell 6 so that the particles pass through the center of the flow cell one by one in line. The particles passing through the flow cell are irradiated with a laser beam, for example, by a laser diode 7, preferably in a direction orthogonal to the flow cell. After penetrating the flow cell, the laser light is stopped by a beam stopper 8. The scattered light is received by a photo acceptance unit 10, for example, a photo diode (FIG. 1). As the laser light, light having a wavelength of 310 to 1285 nm may be used, for example, 488 nm, 680 nm, 780 nm, 860 nm, 980 nm and the like. The scattered light detected may be forward scattered light, side scattered light or both of them.

Figure 2:
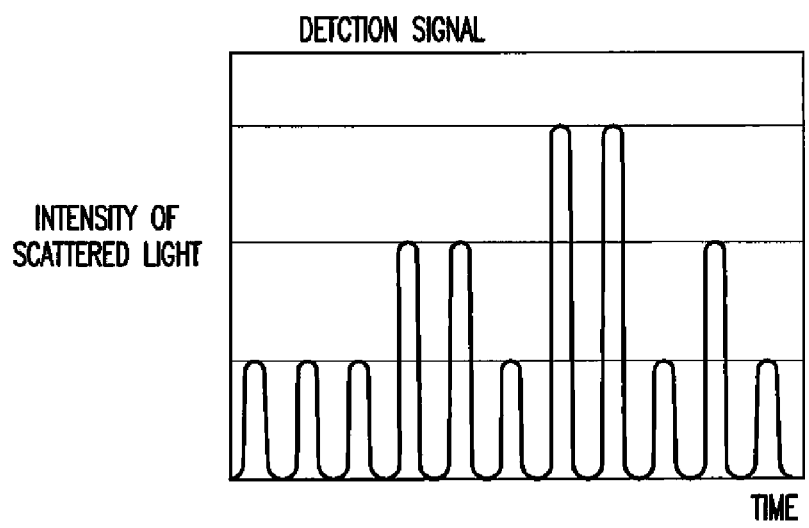
FIG. 2 is a schematic view sowing an electric pulse representative of scattered light generated when particles crosses a laser light, in a whole blood immunoassay in accordance with the present invention.
Figure 3:
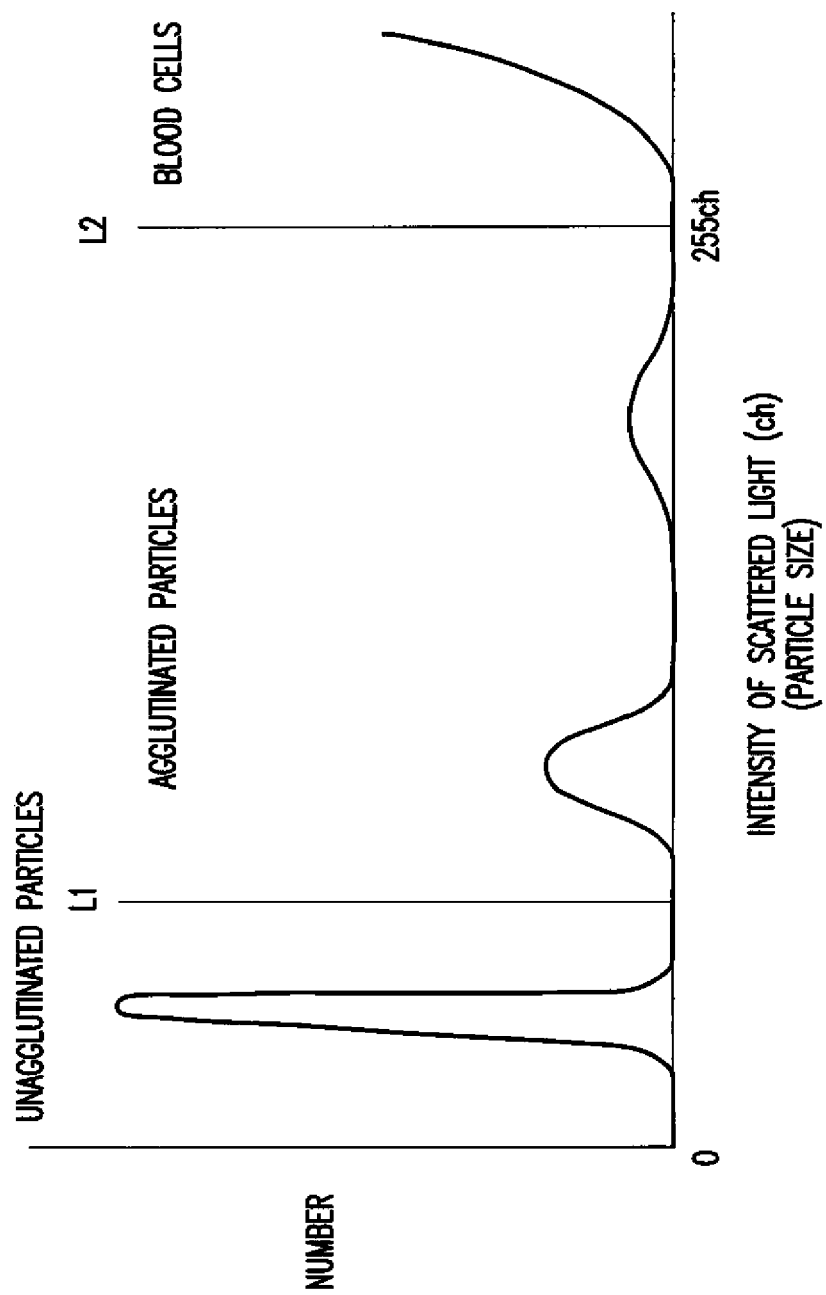
FIG. 3 is a particle size distribution of agglutinated particles in a whole blood immunoassay in accordance with the present invention.

When a particle crosses the laser light, a scattered light pulse is generated which has an intensity according to the volume of the particle. The pulse is received by the photo acceptance unit. Usually, the scattered light pulse received is converted to an electric pulse (FIG. 2). Thereby, information about the particle size distribution of the particles can be obtained. That is, the electric pulse has an intensity according to the volume of the particle entering within the laser light, which particle may be a single particle unagglutinated, two particles agglutinated, three particles agglutinated and the like, blood cells itself, or the like. The electric pulses representative of the volume of particles show a particle size distribution as shown in FIG. 3.

In Step (c), threshold values are set for distinguishing unagglutinated particles, agglutinated particles and blood cells on the basis of the intensity of the scattered light. In the case where the whole blood sample is used, an accurate degree of agglutination cannot be obtained only by distinguishing the unagglutinated particles from the agglutinated particles because blood cell information is included in agglutinated particle information. The unagglutinated particles, agglutinated particles and blood cells have different intensities of forward scattered light because of their different particle sizes, and therefore, they can be distinguished from each other. The threshold values (L1, L2) are set between the unagglutinated particles and the agglutinated particles and between the agglutinated particles and the blood cells for distinguishing the unagglutinated particles from the agglutinated particles and distinguishing the agglutinated particles from blood cells by the intensity of the scattered light, respectively.(see FIG. 3)

The threshold values here may be set as soon as the scattered light of the whole blood sample to be tested itself is measured on the basis of the measured scattered light data; may be set on the basis of the measured scattered light data after obtaining the data; or may be set beforehand as estimated threshold values from known information, accumulated past data or the like. Especially, considering measurement errors and reproducibility, the threshold values are preferably set by establishing the threshold values on measuring the intensity of the scattered light, on the basis of the measured scattered light data.

In Step (d), the unagglutinated particles, agglutinated particles and blood cells are distinguished from each other and counted with reference to the threshold values.

For example, the number of blood cells can be obtained from data exceeding the threshold value (L2) between the agglutinated particles and the blood cells, and the number of the agglutinated particles P can be obtained accurately by subtracting the obtained number of the blood cells from the count of particles on or above the threshold value (L1) between the unagglutinated particles and the agglutinated particles. Or the number of the agglutinated particles P is a count between L1 and L2. The number of the unagglutinated particles M can be obtained by counting the number of particles below L1. It is possible to judge the presence of the antigen or antibody in the whole blood sample from the obtained numbers or counts by use of a method described later or the like.

If particles not to be measured such as chylomicrons are present in the sample, these particles are also included in the particle size distribution of the insoluble carrier particles to be measured. In this case, the particle size distribution of the particles not to be measured can be estimated by interpolation using spline function and subtracted from the particle size distribution including the particles to be measured and the particles not to be measured. Thereby an approximate correction data only of the particles to be measured can be obtained and utilized for calculating accurate counts of the agglutinated particles and the unagglutinated particles (see Japanese Patent No. 2912413).

In the present invention, further in Step (e), the degree of agglutination is calculated. From the calculated degree of agglutination, the concentration of the antigen or antibody may be obtained.

The degree of agglutination may be represented by P/(M+P), wherein P is the number of the agglutinated particles obtained above and M is the number of the unagglutinated particles obtained above. The degree of agglutination is the ratio of the agglutinated particles, which are involved in the antigen/antibody reaction, with respect to all the counted particles.

The concentration of the antigen or antibody may be obtained by use of a calibration curve which is produced beforehand by obtaining the relationship of the degree of agglutination of the antigen or antibody to be measured to a known concentration of the antigen or antibody (preferably, a plurality of degrees of agglutination are determined with changing the concentration).

Also, in Step (f), the concentration of the antigen or antibody in the whole blood sample may be corrected with reference to the count of the blood cells. That is, the concentration of the antigen or antibody obtained in Step (e) reflects the hematocrit content in the whole blood sample and thus is smaller than that obtained using serum. Therefore, the hematocrit content is corrected.

For correction, the number of the blood cells, which is subtracted above, is used. For example, the correction can be carried out by use of the following correction formula:

$$C = CO/(1 - B/A) \quad (I)$$

wherein C is a corrected value, CO is the concentration of the antigen or antibody in the whole blood sample, B is the number of blood cells (value counted above the threshold between the agglutinated particles and the blood cells) and A is a constant. In this connection, constant A can be experimentally obtained from correlation between the hematocrit value and the value counted above the threshold between the agglutinated particles and the blood cells. Constant A corresponds to a value counted when the hematocrit value is supposed to reach 100% (that means that the whole blood sample contains only blood cell component). The ratio of the blood cell component in a collected whole blood sample can be found by calculating B/A.

If the blood cell components of the whole blood sample settle and the fully automated immunoassay apparatus sucks a supernatant plasma component alone, the above-mentioned CO is affected little by hematocrit, and therefore, the correction is not necessary. At this time, since the number of blood cells (B) in the sucked plasma component is small, the B/A of the above formula approaches 0 and the correction is not made. Thus, by use of the method of the present invention, accurate measured values can be calculated even with the whole blood sample.

The above correction formula can be applicable not only to the case where an immunoassay section alone performs an immunoassay and counts blood cells but also to the case where an apparatus provided with both an immunoassay section and a blood cell counting section is used.

Alternatively, in step (g), the concentration of the antigen or antibody in the whole blood sample may be corrected with reference to the MCV (mean corpusculer volume) of erythrocyte and the number of blood cell. The MCV can be obtained, for example, from the scattered lights detected in the step (b), in reference to the threshold values set in the step (c). The correction can be carried out using the following correction formula:

$$C = CO/\{1 - (B/A) \times (MCV/D)\} \quad (II)$$

wherein C, CO, A and B are the same as defined above, MCV is an value of MCV measurement in the sample and D is a constant.

The D is a standard value of MCV measurement and generally around 90 fl, but may be a mean value of MCV measurement of normal samples.

The correction using MCV is not usually required because MCV is usually within the range of 89 to 99 fl. However, exceptional samples have MCVs outside this range. With regard to such samples, the correction (formula (I)) only according to the number of blood cells leaves some errors. Additional correction by the above correction formula (formula (II)) according to MCV can provide a correct measurement regarding a sample with an abnormal MCV.

In the present invention, it is possible to subject not only whole blood samples but also other types of blood samples. The blood samples here include serum samples, plasma samples and the like. Preferably, the sample to be assayed is a plurality of whole blood samples, among which a serum sample is involved.

That is, a serum sample can be subjected to steps corresponding to the above-described steps (a) to (d) for measuring degree of agglutination, the steps (a) to (e), the steps (a) to (f) or steps (a) to (e) and (g).

In the case where a serum sample is subjected to steps corresponding to the above described steps, the serum do not usually contain blood cells, and therefore, few blood cells are counted or only a very small number is obtained if blood cells are counted. In this case, the serum analysis can be carried out using a serum analysis program. Here, the serum analysis program means a program for calculating P/T as degree of agglutination, wherein P is the count of agglutinated particles having been involved in immune reaction, T is the sum of P and M and M is the count of unagglutinated particles or also a program for further calculating the amount of an antigen or an antibody in a sample from the degree of agglutination of the sample using a calibration line obtained beforehand by measuring the degree of agglutination of the antigen or antibody in a known concentration.

The selection of the serum analysis program or the whole blood analysis program is preferably made at an early stage of the immune agglutination reaction. Usually, the selection can be made without any problems after the immune agglutination reaction progresses sufficiently. However, if the concentration of the antigen or antibody in the sample is considerably high, the agglutinated particles may mix with blood cells. In the early stage of the immune agglutination reaction, since the reaction has not progressed sufficiently, agglutinated particles are not taken for blood cells and judgment can be made rapidly. Here, the early stage of the immune agglutination reaction means a period from the start of the reaction until the reaction progresses and reaches equilibrium.

In case where the serum analysis program is used, it is preferable to set a border blood cell number for recognition of either the serum or the whole blood, and recognizing the serum if the number of blood cells is not larger than or below the set border number.

On the other hand, in the case where a whole blood sample is used, a large number of blood cells are counted. Therefore, in this case, the whole blood analysis can be carried out according to the steps (a) to (d), (a) to (e), (a) to (f) or (a) to (e) and (g) using a whole blood analysis program. Here, the whole blood analysis program means a program for, if the amount of the antigen or antibody calculated simply from the degree of agglutination reflects the blood cell components in a whole blood sample and shows a lower value, correcting the calculated amount of the antigen or antibody in consideration of the blood cell components to convert it into a value equivalent to the amount of the antigen or antibody obtained by the serum analysis.

More particularly, the degree of agglutination is obtained by the above steps (a) to (d), steps (a) to (e) or steps (a) to (fe or steps (a) to (e) and (g), the concentration of the antigen or antibody is optionally measured and further the correction can be done with reference to the number of blood cells.

In the present invention, the degree of agglutination and the like are preferably obtained after the reaction reaches the equilibrium in the viewpoint of accurate measurement.

The immunoassay of the present invention is now described in further detail by way of examples.

EXAMPLE 1

Measurement was conducted using PAMIA-50 (produced by Sysmex Corporation) as a measuring apparatus, RAN-REAM (registered) HBsAg (produced by Sysmex Corporation), a HBsAg-negative whole blood sample and a HBsAg-negative serum sample. RANREAM HbsAg is a reagent kit for measuring HBs antigen and includes a latex reagent, a buffer, a sample diluent and a calibrator, among which the latex reagent and the buffer were used in this example. The latex reagent is a 0.5% (w/v) suspension of 0.8 μm polystyrene latex sensitized with an anti-HBs antibody.

Each sample, 10 μL, was mixed with 80 μL of the buffer (pH6) and incubated at 45° C. for a minute. The polystyrene latex sensitized with the anti-HBs antibody, 10 μL, was added thereto to start the reaction at 45° C. In the case where the whole blood sample was used, the amount of the sample was 13 μL for allowing for the hematocrit content.

About 20 seconds after the reaction was started, 19 μL of the reaction mixture were added to 950 μL of a sheath liquid into a 51-fold dilution. The diluted reaction mixture was introduced to an optical detector of PAMIA-50 to measure the agglutination degree P/T (%) (T1).

About 15 minutes after the reaction was started, the agglutination degree P/T (%) (T2) was measured in the same manner as the agglutination degree P/T (%) (T1).

T1 was the agglutination degree in the early stage of the reaction and was used for judging whether or not the sample was within a measurement range. Usually, T2 is used as the agglutination degree (agglutination ratio) of the sample.

The measurement showed unagglutinated particles had a peak of forward scattered light intensity at about 30 channel (ch). The forward scattered light intensity is represented by a channel number (ch). From the forward scattered light intensity distribution, a forward scattered light intensity of 62 ch was set as a threshold for distinguishing the unagglutinated particles from agglutinated particles.

In the case of the whole blood measurement, strong signals were recognized at 255 ch or higher forward scattered light intensity. However, in the case of the serum measurement, almost no signals were recognized at 255 ch or higher. Accordingly, when the agglutination degree was judged on the basis of all signal data about the whole blood sample, a positive judgment was obtained. But, when the agglutination degree was judged by excluding data about 255 ch or higher, a negative judgment was obtained correctly, as shown on Table 1.

TABLE 1

|  | Whole blood | Serum (control) |
| --- | --- | --- |
| The number of unagglutinated particles (0-62 ch) | 108590 | 107943 |
| The number of agglutinated particles ①(62-254 ch) | 456 | 550 |
| The number of agglutinated particles ②(255 ch or more) | 23084 | 24 |
| P/T % (using data ①) | 0.4% (−) | 0.5% (−) |
| P/T % (using data ①& ②) | 21.7% (+) | 0.5% (−) |

From these results, the threshold between the agglutinated particles and blood cells was set at 255 ch, and data about 255 ch or higher were judged as those about blood cells and excluded from the number of agglutinated particles (the number of particles on or above the threshold between the unagglutinated particles and the agglutinated particles). The agglutination degree was determined on the whole blood sample and the serum sample (control) for comparison. The results are shown in Table 2. In addition, a cut-off value was set to 1.5%.

TABLE 2

|  | Whole blood | Judgment | Serum (control) | Judgment |
|---|---|---|---|---|
| Sample 1 | 27.22% | + | 34.98% | + |
| Sample 2 | 13.99% | + | 15.17% | + |
| Sample 3 | 8.93% | + | 9.89% | + |
| Sample 4 | 0.61% | − | 0.62% | − |
| Sample 5 | 0.64% | − | 0.57% | − |
| Sample 6 | 0.57% | − | 0.58% | − |

As seen in the above table, good results were obtained with the judgment agreeing between the whole blood sample and the serum sample.

EXAMPLE 2

A whole blood sample was measured using PAMIA-50 (produced by Sysmex Corporation) as a measuring apparatus and RANREAM FRN (produced by Sysmex Corporation) as a measurement reagent. RANREAM FRN is a reagent kit for measuring ferritin (FRN) antigen and includes a latex reagent, a buffer, a sample diluent and a calibrator. The latex reagent is a 0.5% (w/v) suspension of 0.8 μm polystyrene latex sensitized with an anti-FRN antibody.

The sample, 10 μL, was mixed with 80 μL of the buffer (pH6) and incubated at 45° C. for a minute. The latex reagent sensitized with the anti-FRN antibody, 10 μL, was added thereto to start the reaction at 45° C.

About 20 seconds after the reaction was started, 19 μL of the reaction mixture were added to 950 μL of a sheath liquid into a 51-fold dilution. The diluted reaction mixture was introduced to an optical detector of PAMIA-50 to measure the agglutination degree P/T (%) (T1).

About 15 minutes after the reaction was started, the agglutination degree P/T (%) (T2) was measured in the same manner as the agglutination degree P/T (%) (T1).

The measurement showed that unagglutinated particles had a peak of forward scattered light intensity at about 30 ch. From the forward scattered light intensity distribution, a forward scattered light intensity of 62 ch was determined as a threshold for distinguishing the unagglutinated particles from agglutinated particles.

In the case of the whole blood measurement, strong signals were recognized at 255 ch or higher forward scattered light intensity. However, in the case of the serum measurement, almost no signals were recognized at 255 ch or higher. Accordingly, the threshold between the agglutinated particles and the blood cells was set to 255 ch, data about 255 ch and higher were recognized to be data about blood cells. The numbers of unagglutinated particles, agglutinated particles and blood cells were obtained and P/T (%) was determined from the number of unagglutinated particles and the number of agglutinated particles.

Separately, a calibration curve was produced beforehand by conducting the same measurement using a sample diluent (as a calibrator with a concentration of 0) and a calibrator containing a known concentration of FRN.

The P/T (%) obtained above was converted to a FRN concentration in the whole blood sample using the produced calibration line.

Subsequently, the correction was carried out using the following formula.

$$C = C0/(1 - B/A)$$

Here, A was set to 45,000 from the correlation between the hematocrit value and the number of blood cells obtained beforehand. Table 3 shows measurement results about 20 samples.

TABLE 3

| Sample No. | Conc. in serum (Control) (ng/ml) | Conc. in whole blood (ng/ml) | The number of blood cells | Corrected value (ng/ml) |
|---|---|---|---|---|
| 1 | 145.91 | 71.02 | 21683 | 137.06 |
| 2 | 106.94 | 54.38 | 19492 | 95.93 |
| 3 | 31.21 | 15.99 | 21457 | 30.56 |
| 4 | 45.08 | 22.07 | 21455 | 42.18 |
| 5 | 80.11 | 40.36 | 20495 | 74.12 |
| 6 | 19.93 | 15.89 | 1525 | 16.45 |
| 7 | 43.76 | 23.99 | 20347 | 43.79 |
| 8 | 178.49 | 85.86 | 22794 | 173.99 |
| 9 | 124.49 | 68.50 | 18541 | 116.50 |
| 10 | 24.20 | 15.54 | 17115 | 25.08 |
| 11 | 129.37 | 62.68 | 23975 | 134.15 |
| 12 | 75.68 | 39.21 | 20147 | 71.00 |
| 13 | 132.65 | 65.87 | 21130 | 124.18 |
| 14 | 19.93 | 4.67 | 18934 | 8.06 |
| 15 | 66.40 | 30.33 | 22641 | 61.04 |
| 16 | 38.42 | 20.88 | 19805 | 37.29 |
| 17 | 53.00 | 27.02 | 21414 | 51.55 |
| 18 | 16.07 | 7.98 | 16039 | 12.40 |
| 19 | 7.12 | 3.74 | 19436 | 6.58 |
| 20 | 81.87 | 41.06 | 20231 | 74.60 |

In Sample No. 6, the blood cell components settled and the supernatant was sucked. However, it showed a good results by the correction without exhibiting higher values.

Figure 4:
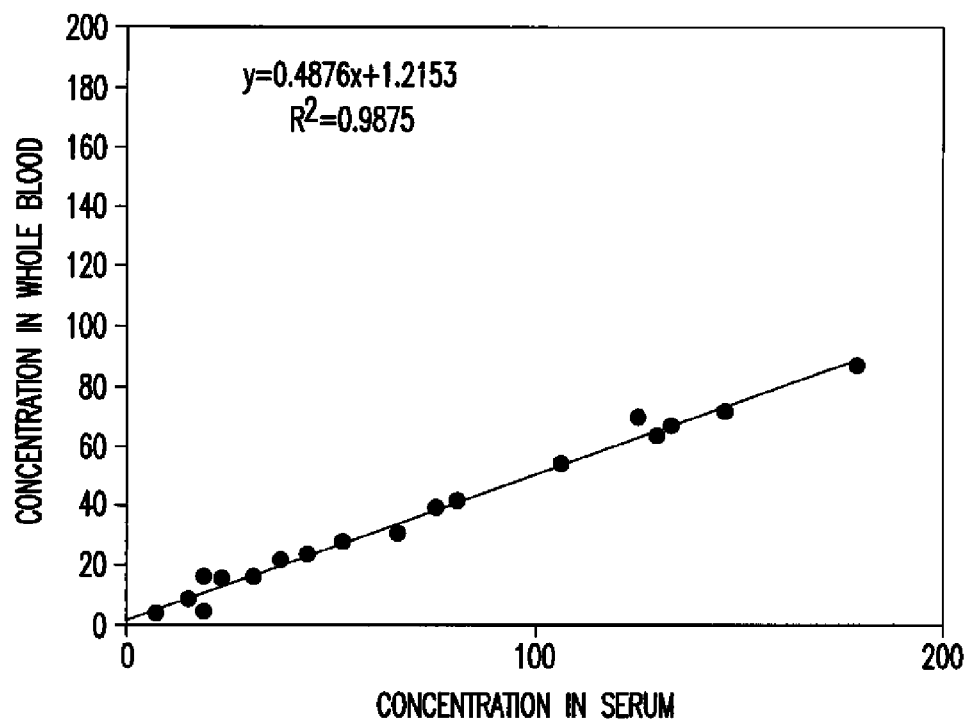
FIG. 4 is a graphical representation showing a correlation between a concentration in serum (control) and a concentration in whole blood (uncorrected) in an example 2 of the present invention.

FIG. 4 is a graphical representation showing a correlation between the concentration in serum (control) and the concentration in whole blood The correlation is good, but the concentration in the whole blood is lower than the concentration in the serum.

Figure 5:
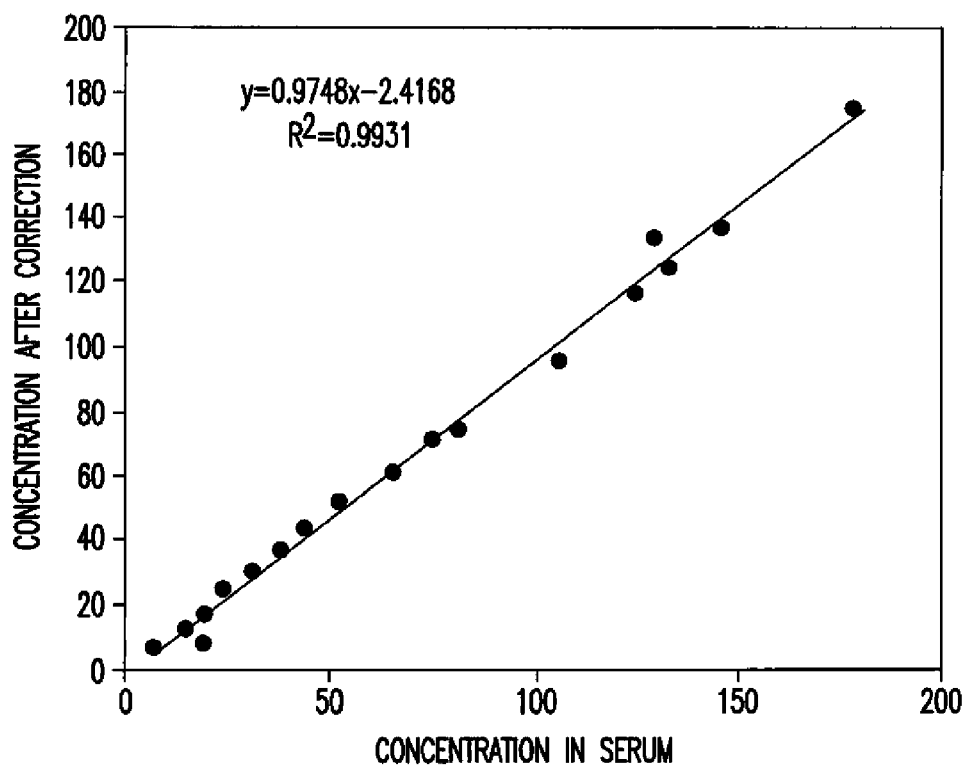
FIG. 5 is a graphical representation showing a correlation between a concentration in serum (control) and a concentration in whole blood (corrected) in an example 2 of the present invention.
Figure 6:
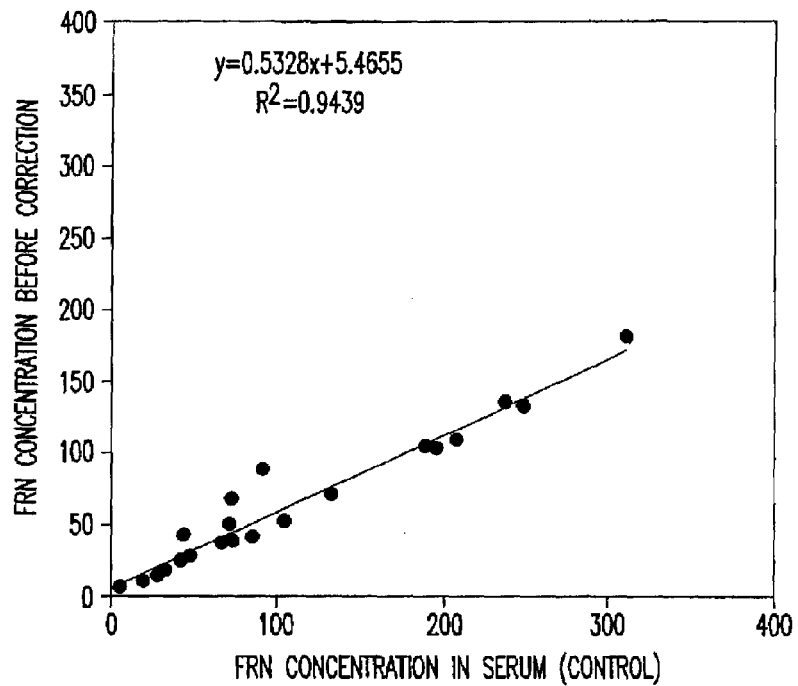
FIG. 6 a graphical representation showing a correlation between a concentration in serum (control) and a concentration in whole blood (uncorrected) in Example 4 of the present invention.
Figure 7:
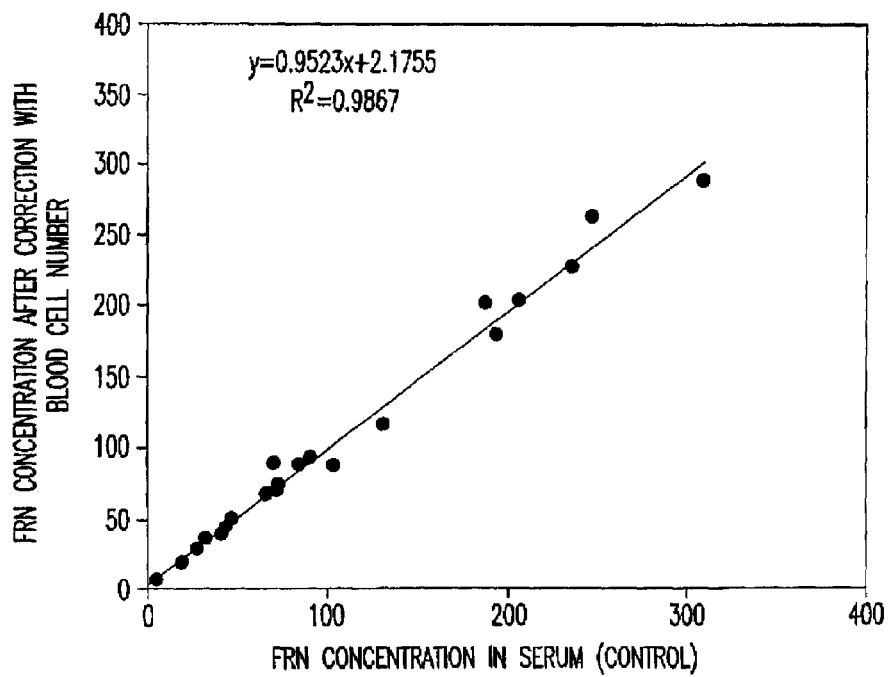
FIG. 7 is a graphical representation showing a correlation between a concentration in serum (control) and a concentration in whole blood (corrected with the number of blood cells alone) in Example 4 of the present invention.
Figure 8:
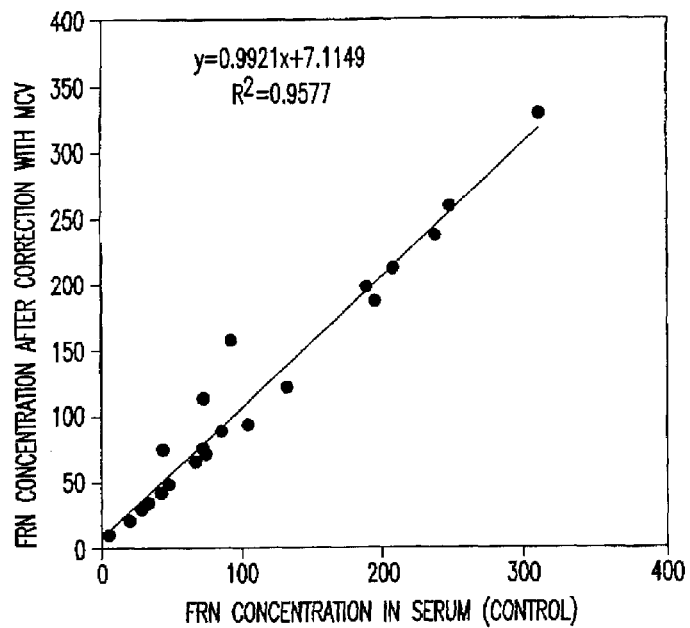
FIG. 8 is a graphical representation showing a correlation between a concentration in serum (control) and a concentration in whole blood (corrected with a hematocrit value) in Example 4 of the present invention.
Figure 9:
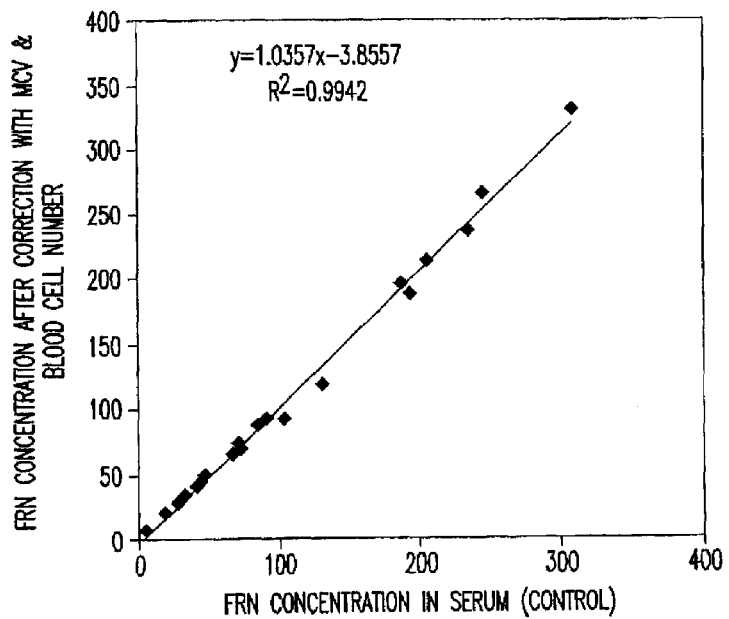
FIG. 9 is a graphical representation showing a correlation between a concentration in serum (control) and a concentration in whole blood (corrected with an MCV value and the number of blood cells) in an example of the present invention.

FIG. 5 is a graphical representation showing a correlation between the concentration in serum and the corrected value. The correlation is good, and the same value as obtained in serum was obtained.

EXAMPLE 3

A whole blood sample and a serum sample were measured using RANREAM HbsAg (produced by Sysmex Corporation) and PAMIA-50 (produced by Sysmex Corporation). RANREAM HbsAg and a latex reagent were the same as used in Example 1.

A calibrator was a solution containing a known concentration of HBsAg and was able to be handled as a serum sample.

Each sample, 10 μL, was mixed with 80 μL of the buffer (pH6) and incubated at 45° C. for a minute. The latex reagent sensitized with the anti-HBs antibody, 10 μL, was added thereto to start the reaction at 45° C.

About 20 seconds after the reaction was started, 19 μL of the reaction mixture were added to 950 μL of a sheath liquid into a 51-fold dilution. The diluted reaction mixture was introduced to an optical detector of PAMIA-50 to measure the agglutination degree P/T (%) (T1).

About 15 minutes after the reaction was started, the agglutination degree P/T (%) (T2) was measured in the same manner as the agglutination degree P/T (%) (T1).

The calibrator and the whole blood sample were measured beforehand, and the threshold for distinguishing unagglutinated particles from agglutinated particles was set at an forward scattered light intensity of 62 ch from the forward scattered light intensity distribution. Also the threshold between agglutinated particles and blood cells was set at 255 ch.

The border blood cell number for selecting the serum analysis program or the whole blood analysis program was set to 200 (number counted regarding 255 ch or higher).

The serum/whole blood judgment for selecting the serum analysis program or the whole blood analysis program may be conducted after the immune agglutination reaction progresses sufficiently, but in this example, the judgment was conducted when T1 was measured. When T1 was measured, the immune agglutination reaction did not progress sufficiently and it was unlikely that data about agglutinated particles by the immune reaction were mixed with data about 255 ch or higher, especially when the concentration of the antigen or antibody in the sample is considerably high. Thus, it was advantageous to make the judgment in the early stage of the reaction.

Next, five whole blood samples and five serum samples were measured at random and the judgment was made. The results are shown in Table 4. In the "judgment" column of Table 4, "serum" is entered when a sample was judged as a serum sample and the serum analysis program was used, and "whole blood" is entered when a sample was judged as a whole blood sample and the whole blood analysis program was used.

TABLE 4

| Sample No. | Count about 255 ch | Judgment |
|---|---|---|
| No.1 (Serum) | 49 | Serum |
| No.2 (Whole blood) | 16366 | Whole blood |
| No.3 (Whole blood) | 15653 | Whole blood |
| No.4 (Serum) | 18 | Serum |
| No.5 (Serum) | 27 | Serum |
| No.6 (Serum) | 25 | Serum |
| No.7 (Whole blood) | 18196 | Whole blood |

TABLE 4-continued

| Sample No. | Count about 255 ch | Judgment |
|---|---|---|
| No.8 (Whole blood) | 17754 | Whole blood |
| No.9 (Whole blood) | 13864 | Whole blood |
| No.10 (Serum) | 45 | Serum |

As seen in the above table, the judgment of "serum" or "whole blood" was correctly made with regard to all the samples. On the basis of this judgement, the serum analysis program or the whole blood analysis program was selected and the agglutination degree was calculated according to the selected analysis program.

EXAMPLE 4

The measurement was carried out on 21 whole blood samples including a sample with an abnormal MCV in the same manner as in Example 2. The MCV and Hct (hematocrit) values were obtained beforehand using a fully automated blood cell analyzer XE-2100 (produced by Sysmex Corporation).

The obtained measurements were handed as follows:
Not corrected (Conc. of FRN),
Corrected only with the number of blood cells ($C=CO/(1-B/A)$) (Corrected by blood number),
Corrected using the hematocrit value ($C=CO/(1-Hct)$) (Corrected by HCT),
Corrected with the MCV and the number of blood cells ($C=CO/\{1-(B/A)\times(MCV/D)\}$) (Corrected by MCV & blood number).

In this example, A was calculated to be 46000 from the correlation between the hematocrit value and the number of blood cells. D was set to 90.

The measurement results are shown in Table 5.

TABLE 5

| | Conc. of FRN in serum | In Whole blood | | | | Corrected by | | |
|---|---|---|---|---|---|---|---|---|
| | | HCT | MCV | Conc. of FRN | 255 ch or more | blood number | HCT | MCV & blood number |
| 1 | 104.72 | 44.3% | 97.4 | 51.69 | 18541 | 86.59 | 92.80 | 91.68 |
| 2 | 48.09 | 42.4% | 88.1 | 27.35 | 20808 | 49.94 | 47.48 | 49.08 |
| 3 | 132.69 | 41.5% | 93.7 | 70.40 | 17759 | 114.67 | 120.34 | 117.71 |
| 4 | 189.19 | 47.1% | 87.5 | 103.73 | 22083 | 199.51 | 196.09 | 194.52 |
| 5 | 28.71 | 52.5% | 91.0 | 13.88 | 23506 | 28.39 | 29.22 | 28.72 |
| 6 | 72.84 | 40.2% | 91.8 | 67.28 | 1227 | 69.12 | 112.51 | 69.16 |
| 7 | 195.49 | 44.6% | 95.9 | 102.52 | 19440 | 177.55 | 185.05 | 186.50 |
| 8 | 44.53 | 42.4% | 93.8 | 42.16 | 1208 | 43.29 | 73.19 | 43.34 |
| 9 | 67.48 | 43.0% | 89.2 | 36.97 | 20408 | 66.46 | 64.87 | 65.99 |
| 10 | 71.74 | 33.1% | 66.7 | 49.63 | 20154 | 88.34 | 74.17 | 73.50 |
| 11 | 85.71 | 53.6% | 89.6 | 40.78 | 24520 | 87.33 | 87.89 | 86.89 |
| 12 | 73.70 | 46.0% | 89.5 | 38.00 | 21835 | 72.33 | 70.36 | 71.97 |
| 13 | 311.42 | 44.9% | 110.2 | 179.96 | 17051 | 285.96 | 326.85 | 329.53 |
| 14 | 237.78 | 42.6% | 95.7 | 135.21 | 18380 | 225.18 | 235.55 | 235.09 |
| 15 | 42.37 | 40.4% | 95.3 | 24.25 | 17723 | 39.44 | 40.68 | 40.96 |
| 16 | 33.41 | 47.7% | 86.3 | 17.71 | 23220 | 35.76 | 33.86 | 34.32 |
| 17 | 207.99 | 48.4% | 95.5 | 108.61 | 21223 | 201.65 | 210.49 | 212.79 |
| 18 | 91.70 | 43.6% | 95.4 | 88.14 | 1799 | 91.73 | 156.28 | 91.95 |
| 19 | 248.52 | 48.6% | 91.4 | 132.09 | 22654 | 260.27 | 256.99 | 264.26 |
| 20 | 5.88 | 34.4% | 86.6 | 6.58 | 1674 | 6.83 | 10.03 | 6.82 |
| 21 | 19.81 | 48.2% | 99.4 | 10.49 | 20343 | 18.81 | 20.26 | 20.51 |

FIGS. 6 to 9 are graphical representations showing correlations with the concentration in serum plotted as control.

The correlation before correction (FIG. 6) has a small inclination owing to influence of the blood cell components. A sample with settled blood cell components has a far higher value.

In the correlation after correction with the number of blood cells (FIG. 7), the influence of the hematocrit value is corrected and the inclination approaches to 1. Although there is practically no problem with this correlation, a sample with a low MCV value has a little higher value and a sample with a high MCV value has a litter lower value.

In the correlation after correction with the hematocrit value (FIG. 8), the influence of the hematocrit value is corrected and the inclination approaches to 1. A sample with settle blood cell components is mistakenly corrected to have a far higher value.

In the correlation after correction with the MCV value and the number of blood cells, the influence of the hematocrit value is corrected and the inclination approached to 1. This shows the best correlation, and even the sample with an abnormal MCV and the sample with settled blood cell components are properly corrected.

According to the present invention, whole blood itself can be used as a sample without pre-treatment, and an accurate and simple immunoassay can be realized.

Also, according to the present invention, in the whole blood immunoassay, the concentration of an antigen or antibody in whole blood can be easily corrected to the same value as the concentration in serum without need to measure the hematocrit value separately.

Further, where blood cell components in a sample settle, the correction can be made without being affected by that.

Also, by simultaneously measuring the concentration of an antigen or antibody and counting blood cells in a whole blood sample and correcting the concentration of the antigen or antibody by the correction formula using the count of blood cells, it is possible to eliminate the influence by decrease of the plasma component due to a blood cell volume in the sample, the influence being such that the concentration of the antigen or antibody is calculated to be a lower value. Thus, accurate measurements can be obtained.

Furthermore, according to the present invention, it is possible to measure a sample without need to pay attention to the type of the sample, that is, a whole blood type or a serum type. Also, since the type of each sample need not be input, errors in inputting can be avoided, and also an analysis program can be properly selected as suitable for each sample. Thus, the reliability and accuracy of measurement results can be improved.

The invention claimed is:

1. An immunoassay for assaying a target antigen or antibody present in serum or plasma portion of a whole blood sample, comprising the steps of:
    (a) mixing the whole blood sample with insoluble carrier particles which are sensitized with an antigen against the target antibody or an antibody against the target antigen, wherein said particles are smaller than erythrocytes, to cause an immune agglutination reaction resulting in an immune agglutination reaction mixture comprising agglutinated insoluble carrier particles and unagglutinated insoluble carrier particles;
    (b) introducing the immune agglutination reaction mixture to a flow cell, irradiating the particles passing through the flow cell with laser light, and detecting scattered light generated thereby;
    (c) setting a first threshold value for distinguishing unagglutinated insoluble carrier particles from agglutinated insoluble carrier particles and a second threshold value for distinguishing the agglutinated insoluble carrier particles from blood cells with regard to intensity of the scattered light;
    (d) distinguishing and counting the unagglutinated insoluble carrier particles, the agglutinated insoluble carrier particles and the blood cells from the intensity of the scattered light detected in the step (b), in reference to the first and second threshold values set in the step (c);
    (e) calculating a degree of agglutination from the number of the unagglutinated insoluble carrier particles and the number of the agglutinated insoluble carrier particles;
    (f) converting the degree of agglutination into a concentration of the target antigen or antibody in the whole blood sample using a calibration curve showing a relationship between a degree of agglutination and a concentration of a target antigen or antibody; and
    (g) obtaining a corrected concentration of the target antigen or antibody based on the following formula:

$C = CO/(1 - B/A)$, wherein C is a corrected concentration, CO is the concentration of the target antigen or antibody present in the serum or plasma portion of whole blood sample, B is the number of blood cells and A is a constant.

2. The immunoassay according to claim 1, wherein the scattered light is forward scattered light.

3. The immunoassay according to claim 1, wherein the size of the insoluble carrier particles is 0.1 µm to 1.0 µm.

4. The immunoassay according to claim 1, wherein, in the step (a), the temperature is from 20 to 50° C. and the time is from 15 seconds 20 minutes.

5. An immunoassay for assaying a target antigen or antibody present in serum or plasma portion of a whole blood sample, comprising the steps of:
    (a) mixing the whole blood sample with insoluble carrier particles which are sensitized with an antigen against the target antibody or an antibody against the target antigen, wherein said particles are smaller than erythrocytes, to cause an immune agglutination reaction resulting in an immune agglutination reaction mixture comprising agglutinated insoluble carrier particles and unagglutinated insoluble carrier particles;
    (b) introducing the immune agglutination reaction mixtures to a flow cell, irradiating the particles passing through the flow cell with laser light, and detecting scattered light generated thereby;
    (c) setting a first threshold value for distinguishing unagglutinated insoluble carrier particles from agglutinated insoluble carrier particles and a second threshold value for distinguishing the agglutinated insoluble carrier particles from blood cells, with regard to intensity of the scattered light;
    (d) distinguishing and counting the unagglutinated insoluble carrier particles, the agglutinated insoluble carrier particles and the blood cells from the intensity of the scattered light detected in the step (b), in reference to the first and second threshold values set in the step (c);
    (e) calculating a degree of agglutination from the number of the unagglutinated insoluble carrier particles and the number of the agglutinated insoluble particles;
    (f) converting the degree of agglutination into a concentration of the target antigen or antibody in the whole blood sample using a calibration curve showing a relationship between a degree of agglutination and a concentration of target antigen or antibody; and (g) obtaining a mean corpusculer volume (MCV) in the whole blood sample, wherein the concentration of the target antigen or antibody present in the whole blood sample is corrected according to the MCV measurement and the number of blood cells.

6. The immunoassay according to claim 5, wherein the mean corpusculer volume (MCV) is obtained from the scattered lights detected in the step (b), in reference to the threshold values set in the step (c).

7. The immunoassay according to claim 5, wherein correction according to the MCV measurement and the number of blood cells is made by use of the following formula:

$$C=CO/\{1-(B/A) \times (MCV/D)\},$$

wherein C is a corrected concentration, CO is the concentration of the target antigen or the target antibody present in the serum or plasma portion of whole blood sample, A is a constant, B is the number of blood cells, MCV is the MCV measurement of the sample, and D is a constant.

8. The immunoassay according to claim 5, wherein the scattered light is forward scattered light.

9. The immunoassay according, to claim 5, wherein the size of the insoluble carrier particles is 0.1 µm to 1.0 µm.

10. The immunoassay according to claim 5, wherein, in the step (a), the temperature is from 20 to 50° C. and the time is from 15 seconds to 20 minutes.

* * * * *